United States Patent [19]

Kochi et al.

[11] Patent Number: 4,778,785

[45] Date of Patent: Oct. 18, 1988

[54] PHARMACEUTICAL COMPOSITION FOR RETARDING AND REDUCING CACHEXIA

[75] Inventors: Mutsuyuki Kochi, Matsudo; Shinichiro Esumi, Kunitachi; Setsuo Takeuchi, Higashiyamato, all of Japan

[73] Assignees: Kaken Pharmaceutical Co., Ltd.; Rikagaku Kenkyusho, both of Tokyo, Japan

[21] Appl. No.: 902,293

[22] Filed: Aug. 29, 1986

[30] Foreign Application Priority Data

Sep. 6, 1985 [JP] Japan .................................. 60-196945

[51] Int. Cl.4 ....................... A61K 31/11; A61K 31/70
[52] U.S. Cl. ......................................... 514/23; 514/27; 514/35; 514/699
[58] Field of Search ..................... 568/425; 514/23, 27, 514/35, 699; 536/18.1

[56] References Cited

U.S. PATENT DOCUMENTS

| 4,444,791 | 4/1984 | Simon ................................... 514/691 |
| 4,613,588 | 9/1986 | Katayama et al. ..................... 514/23 |
| 2343475 | 10/1977 | France ........................ A61K 31/11 |

OTHER PUBLICATIONS

Moley, J. et al: Chemical Abstracts vol. 100:18155x (1984).
Takeuchi et al; Chemical Abstracts 92:110676g (1980)
Takeuchi et al; Chemical Abstracts 90:142177v (1979)
Miyao; Chemical Abstracts 89:117794r (1978)
Takeuchi et al; Agric. Biol. Chem. 42(7):1149–51 (1978)

*Primary Examiner*—Ronald W. Griffin
*Assistant Examiner*—Nancy S. Carson
*Attorney, Agent, or Firm*—Bucknam and Archer

[57] ABSTRACT

A pharmaceutical composition for retarding and reducing cachexia comprising, as an efficacious ingredient, at least one compound selected from the group consisting of benzaldehyde and 4,6-O-benzylidene-D-glucose, and a method for retarding and reducing cachexia in humans which comprises administering to an affected human at least one said compound.

5 Claims, No Drawings

PHARMACEUTICAL COMPOSITION FOR RETARDING AND REDUCING CACHEXIA

BACKGROUND OF THE INVENTION

1. Field of the Invention

The present invention relates to a pharmaceutical composition for retarding and reducing cachexia and a method of retarding and reducing cachexia by the administration of the pharmaceutical composition.

"Cachexia" is a condition of general poor health, the main symptoms of which are progressive weight loss, anemia, drying of skin and anorexia. Known examples of this disease include cancerous cachexia, cachexia collagenosis, hypophysical cachexia, cachexia ovariopriva and cachexia thyroidea.

In the case of cancerous cachexia, a person with cancer dies with no symptoms of rupture or mechanical compression of an important organ, no bleeding nor infection.

2. Description of the Prior Art

In accordance with the known treatment for retarding or reducing cachexia, efforts have been made to recover the nutritive conditions of a patient, for example, by blood transfusion or liquid infusion. However, the known treatments are not satisfactory in that complete cure of the disease cannot be achieved.

Benzaldehyde and 4,6-O-benzylidene-D-glucose have been known in the art and already used as medicines because they exhibit carcinostatic functions. (In this connection, reference should be made to Japanese Patent Laid-Open Publication Nos. 108027/1977 and 70428/1979.) However, it was not known that these compounds have a pharmaceutical function, i.e. the function of curing cachexia, as taught by the present invention.

Although European Patent Application No. 0166 443 discloses the use of benzaldehyde or 4,6-O-benzylidene-D-glucose for the preparation of a pharmaceutical composition for inhibiting enkephalinase in humans, this prior art does not teach the properties as utilized in this invention.

On the other hand, a method and/or pharmaceutical composition for curing cachexia is known from U.S. Pat. Nos. 4,110,437 and 4,444,791. U.S. Pat. No. 4,110,437 teaches the use of hydrazine sulfate, and U.S. Pat. No. 4,444,791 teaches the use of friedelan-3-one. These compounds are quite different from the compounds used in this invention, as will be apparent to those skilled in the art.

SUMMARY OF THE INVENTION

After strenous efforts to discover ways to improve the methods for combating cachexia, we have developed an invention based on the finding that benzaldehyde and/or 4,6-O-benzylidene-D-glucose are effective in retarding and reducing cachexia, particularly cancerous cachexia.

More specifically, the present invention provides a pharmaceutical composition for retarding and reducing cachexia which comprises, as an effective ingredient, at least one compound selected from the group consisting of benzaldehyde and 4,6-O-benzylidene-D-glucose, and a method of retarding and reducing cachexia by the administration of said pharmaceutical composition.

DETAILED DESCRIPTION OF THE INVENTION

Benzaldehyde and 4,6-O-benzylidene-D-glucose are known compounds represented, respectively, by the following chemical formulae of:

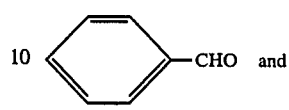

Benzaldehyde

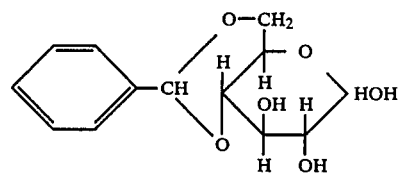

4,6-O—Benzylidene-D-glucose

Benzaldehyde and 4,6-O-benzylidene-D-glucose have such extremely low toxicities that the acute toxicity level $LD_{50}$ of the former is 5 g/kg and that of the latter is 4 g/kg, as determined by the subcutaneous injection of rats, and thus it is very safe to use.

The pharmaceutical composition for retarding and reducing cachexia, according to this invention, may be used in the form of an injection, instillation, tablet, capsule, granule, powder or suppository. The composition may be prepared so as to have any of the desired formulations by conventional processes. Any of the known adjuvants, including stabilizers, which have been conventionally used in the art, may be mixed with the composition of the invention, or the composition of the invention may be covered with a coating.

In case where benzaldehyde is used as the effective ingredient, according to this invention, it is preferred that the compound is used in the form of an inclusion compound, for example, with cyclodextrin, since benzaldehyde is an unstable and irritative compound.

The pharmaceutical composition for retarding and reducing cachexia, according to this invention, may be administered through intravenous or subcutaneous injection, or by oral or rectal application.

The proper dosage amount of the pharmaceutical composition of this invention varies depending on the age, body weight and disease level of a patient and also depending on the method of administration. In view of the clinical data and the results of acute toxicity tests, the preferable daily dosage amount given to an adult patient ranges from 50 to 5000 mg either for the single use of benzaldehyde or 4,6-O-benzylidene-D-glucose or for the combined use of both. The daily dose may be administered all at once or in several doses a day.

Some formulation examples will be described hereinbelow. However, it is noted here that the present invention is not limited only to the following examples.

FORMULATION EXAMPLE 1 (INJECTIONS AND INFUSIONS)

Benzaldehyde and powdered glucose were aseptically placed into vials so that each vial contained 500 mg of benzaldehyde and 5 g of powdered glucose.

These vials were then sealed and then filled with an inert gas, such as nitrogen or helium, and thereafter stored in a dark, cold place. Before use, 100 ml of a 0.85% physiological saline solution was added to prepare an intravenous injection.

FORMULATION EXAMPLE 2 (INJECTIONS AND INFUSIONS)

Intravenous injections similar to those in Formulation Example 1 were prepared, except that 4,6-O-benzylidene-D-glucose was used in place of benzaldehyde.

FORMULATION EXAMPLE 3 (CAPSULES)

A mixture of 30 mg of benzaldehyde dissolved in 1 g of refined sesame oil and 100 mg of aluminium stearate gel was placed into capsules, in amounts of 0.5 ml respectively, to prepare capsules to be administered orally.

FORMULATION EXAMPLE 4 (CAPSULES)

200 mg of 4,6-O-benzylidene-D-glucose was placed into capsules to prepare capsules to be administered orally.

FORMULATION EXAMPLE (ENTERIC TABLETS)

33 g of benzaldehyde was added to 3,000 ml of a saturated aqueous solution of $\beta$-cyclodextrin (produced by Nihon Shokuhin Kako Co., Ltd.), and mixed by stirring for 5 hours, whereby an inclusion compound precipitated. The precipitated inclusion compound was dried under reduced pressure to obtain about 300 g of a dried inclusion compound, the resulting product of this Example.

1,000 tablets for each of the enteric tablets (a) and (b) having the following compositions were prepared.

|  | (a) | (b) |
|---|---|---|
| (A) | | |
| Main Ingredient (Inclusion Compound Containing 8.5% of Benzaldehyde) | 300 (g) | 150 (g) |
| Lactose | 298.2 | 149.1 |
| Hydroxypropyl Cellulose | 1.8 | 0.9 |
| Magnesium Stearate | 6.0 | 3.0 |
| (B) | | |
| Cellulose Acetate Phthalate | 18.0 (g) | 12.0 (g) |
| Hydroxypropylmethyl Cellulose Phthalate | 18.0 | 18.0 |

Each of the compositions (A) was taken and thoroughly mixed, and the mixture was then either directly compressed or intimately kneaded. To prepare the tablets, the compressed or kneaded mixture was granulated by passing the mixture through a sieve fitted with an extruder for granulation, and then thorough dried and compressed.

Each of the molded tablets was coated with the composition (B) by applying the tablet with a uniform solution of either one of the compositions (a) or (b).

FORMULATION EXAMPLE 6 (ENTERIC TABLETS)

Enteric tablets were prepared generally following the procedures described in Formulation Example 5, except that 15 g of 4,6-O-benzylidene-D-glucose was used in place of benzaldehyde.

CLINICAL EXAMPLES

Patients affected by cachexia were treated by administering, in accordance with this invention, benzaldehyde and/or 4,6-O-benzylidene-D-glucose as described in detail in the following Clinical Examples 1 to 3.

Clinical Example 1

Patient: Female, 48 years old
Diagnosis: Cancer in right ovary, Cachexia caused by metastasis of cancer to peritoneum and liver (1) Before Administration of 4,6-O-Benzylidene-D-glucose:

Although the adbomen of the patient was opened by an abdominal operation, it was impossible to remove the diseased portions and thus the abdomen was closed without extracting the affected portions. The patient could eat very little and thus was supplied with nutritive substances by instillations every day. The body weight of the patient decreased to 29 kg, and she was confined to bed.

Chemotherapy was tried to administering mitomycin, 5-fluorouracil and cytarabine. However, the use of these medicines caused intensive adverse reactions, such as anorexia, nausea and Leukopenia (decrease in number of leucocytes), and as the cachexia grew worse and worse, the patient became extremely emaciated. For these reasons, chemotherapy was stopped after three weeks.

(2) Course of Administration of 4,6-O-Benzylidene-D-glucose:

First day: 1,200 mg of 4,6-O-benzylidene-D-glucose dissolved in a physiological saline solution through an intravenous injection once a day was administered.

Eighth Day: Nausea disappeared, and the patient could take meals. Frequency of urination decreased to 6 to 8 times a day. (Urination frequencies before administration of the composition had been 15 to 20 times a day.)

Nineteenth Day: The patient could sit up in bed.

Thirtieth Day: cachexia symptoms were alleviated, and the patient could walk, although in view of the result of a CT scan examination, it was seen that the dimensions of the tumor had not been reduced.

Fifty-sixth Day: The cancer of the liver (left) was slightly reduced. No change was observed in connection with the cancer in other portions. The symptoms of cachexia disappeared completely, and the body weight of the patient increased to 31 kg. the patient became capable of doing light work, such as domestic duties, and she was released from hospital.

Eighty-fifth Day: The body weight of the patient increased to 35 kg.

Clinical Example 2

Patient: Male, 68 years old
Diagnosis: Symptoms of cachexia due to lung cancer (1) Before Administration of Benzaldehyde and 4,6-O-Benzylidene-D-glucose:

Chest pains, dyspnea, coughing, discharge of phlegm were observed.

Through the use of X-ray photography, the presence of a tumor having dimensions corresponding to a hen's egg at the lobus inferior of the Pulmo sinister was shown, as was the presence of fluid in the thoracic cavity. Thus, it was diagnosed that he should be sent to a hospital. The patient had no appetite, progressive cachexia, and he could continue breathing only in a squating position while being given oxygen. The body weight of the patient was 47 kg.

(2) Course of Administration of Benzaldehyde and 4,6-O-Benzylidene-D-glucose:

First Day: The tablets prepared in the Formulation Example 5, each tablet containing 25 mg of benzaldehyde, at a dosage of 5 tablets, 4 times a day, were administered. 1,200 mg of 4,6-O-benzylidene-D-glucose dissolved in a physiological saline solution through intravenous injection once a day was also administered.

Afer the Lapse of One Month: The patient recovered his appetite, and with the reduction of chest pain, he could breathe easily. The dimensions of the diseased portion in the lung were not changed.

After the Lapse of Two Months: Almost all of the symptoms caused by cachexia were alleviated, and the body weight of the patient increased to 52 kg. The patient recovered his ability to walk.

After the Lapse of Three Months: The patient had recovered his normal appetite. The fluid in the thoracic cavity disappeared. The symptoms due to cachexia, including complaints of languor, disappeared completely, and the patient could begin light work, such as office duties. An X-ray photographic examination revealed no change in the dimensions of the affected portion.

Clinical Example 3

Patient: Male, 77 years old
Diagnosis: Symptoms of cachexia due to lung cancer (the type of cancerous tissue not being specified)

(1) Before Administration of Benzaldehyde

The patient had no appetite, and abnormalities were observed in the function of this liver (Glutamic Acid Oxaloacetic Acid Transaminase (GOT): 120, Glutamic Acid Pyruvic Acid Transaminase (GPT): 98, α-fetoprotein (AFP): 20,000 ng/ml). Through CT scan and echo examinations, a total of four tumors were observed, one having the dimensions of 7 cm×7 cm and each of the other three metastasized tumors having a diameter of about 1 cm. Severe symptoms due to cachexia were found.

(2) Course of Administration of Benzaldehyde:

First Day: The symptoms due to cachexia were growing worse. 25 mg benzaldehyde tablets prepared in Formulation Example 5 were adminstered at a dosage of 5 tablets, 4 times a day.

As set forth in Table 1, the patient recovered his appetite after a period of one month, and the values of AFP, GOT and GPT lowered favorably every month unitl they reached normal levels.

Almost all of the symptoms due to cachexia disappeared after the lapse of three months, and the body weight of the patient began to increase.

TABLE 1

|  | AFP | GOT | GPT | Body weight (kg) | Precipitation of Blood |
|---|---|---|---|---|---|
| Before Dosage | 20,000 | 120 | 98 | 46 | 78 |
| One Month Dosage | 15,000 | 87 | 70 | 46 | 60 |
| Two Month Dosage | 7,700 | 72 | 40 | 46 | 48 |
| Three Month Dosage | 2,200 | 38 | 35 | 47 | 40 |

Although the present invention has been described by referring to preferred compositions and methods for retarding and reducing cachexia, it should be noted that the present invention should not be limited solely to the examples described but that the scope of the invention is defined only by the appended claims.

What is claimed is:

1. A method for retarding and reducing cachexia in humans which comprises administering to an affected human at least one compound selected from the group consisting of benzaldehyde and 4,6-O-benzylidene-D-glucose in an effective dosage sufficient to retard and reduce the cachexia.

2. The method according to claim 1, in which at least one compound selected from the group consisting of benzaldehyde and 4,6-O-benzylidene-D-glucose is administered orally in unit dose.

3. The method according to claim 1, in which at least one compound selected from the group consisting of benzaldehyde and 4,6-O-benzylidene-D-glucose is administered parenterally.

4. The method according to claim 1, wherein the daily dosage of at least one compound selected from the group consisting of benzaldehyde and 4,6-O-benzylidene-D-glucose is from 50 to 5,000 mg.

5. The method according to claim 1, wherein the cachexia is cancerous cachexia.

* * * * *